(12) United States Patent
McHale et al.

(10) Patent No.: US 9,149,528 B2
(45) Date of Patent: Oct. 6, 2015

(54) TOPICAL VITAMIN D ORAL SUPPLEMENT COMPOSITIONS

(71) Applicant: Premier Dental Products Company, Plymouth Meeting, PA (US)

(72) Inventors: William A. McHale, Collegeville, PA (US); Dale G. Brown, Wharton, TX (US)

(73) Assignee: Premier Dental Products Company, Plymouth Meeting, PA (US)

( * ) Notice: Subject to any disclaimer, the term of this patent is extended or adjusted under 35 U.S.C. 154(b) by 0 days.

(21) Appl. No.: 13/650,963

(22) Filed: Oct. 12, 2012

(65) Prior Publication Data

US 2013/0095154 A1    Apr. 18, 2013

Related U.S. Application Data

(60) Provisional application No. 61/546,811, filed on Oct. 13, 2011.

(51) Int. Cl.
| | |
|---|---|
| *A61K 9/107* | (2006.01) |
| *A61P 29/00* | (2006.01) |
| *A61K 31/59* | (2006.01) |
| *A61P 1/02* | (2006.01) |
| *A61K 47/10* | (2006.01) |
| *A61K 9/00* | (2006.01) |
| *A61K 47/24* | (2006.01) |
| *A61K 47/26* | (2006.01) |
| *A61K 9/06* | (2006.01) |
| *A61K 31/593* | (2006.01) |
| *A61C 15/04* | (2006.01) |
| *A61C 19/06* | (2006.01) |
| *A61K 8/34* | (2006.01) |
| *A61K 8/67* | (2006.01) |
| *A61Q 11/00* | (2006.01) |
| *A61K 8/891* | (2006.01) |
| *A61K 8/90* | (2006.01) |

(52) U.S. Cl.
CPC .............. *A61K 47/10* (2013.01); *A61C 15/041* (2013.01); *A61C 19/063* (2013.01); *A61K 8/345* (2013.01); *A61K 8/67* (2013.01); *A61K 8/891* (2013.01); *A61K 8/90* (2013.01); *A61K 9/006* (2013.01); *A61K 9/0063* (2013.01); *A61K 9/06* (2013.01); *A61K 31/593* (2013.01); *A61K 47/24* (2013.01); *A61K 47/26* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,442,842 A | 5/1969 | Bonin | |
| 4,652,441 A | 3/1987 | Okada et al. | |
| 4,711,782 A | 12/1987 | Okada et al. | |
| 5,437,857 A | 8/1995 | Tung | |
| 5,651,959 A * | 7/1997 | Hill et al. | ............ 424/49 |
| 5,665,374 A | 9/1997 | Hill et al. | |
| 5,665,382 A | 9/1997 | Grinstaff et al. | |
| 5,925,595 A | 7/1999 | Seitz et al. | |
| 6,534,091 B1 | 3/2003 | Garces Garces et al. | |
| 2002/0090398 A1 | 7/2002 | Dunn et al. | |
| 2004/0258634 A1 | 12/2004 | Cazor et al. | |
| 2008/0039434 A1* | 2/2008 | Colli | ............ 514/167 |
| 2008/0095719 A1 | 4/2008 | Herrmann et al. | |
| 2008/0152598 A1 | 6/2008 | Basic | |
| 2008/0175918 A1 | 7/2008 | Laulicht | |
| 2008/0295960 A1 | 12/2008 | Schalau, II et al. | |
| 2009/0087501 A1 | 4/2009 | Cummins | |
| 2011/0104052 A1 | 5/2011 | Barnett et al. | |
| 2011/0118217 A1 | 5/2011 | Gudmundsson et al. | |
| 2012/0171128 A1* | 7/2012 | Ramirez | ............ 424/48 |

FOREIGN PATENT DOCUMENTS

| | | |
|---|---|---|
| WO | 9639116 A1 | 12/1996 |
| WO | WO 2007/036802 | 4/2007 |
| WO | 2007099398 A1 | 9/2007 |

OTHER PUBLICATIONS

McMahon et al. "Vitamin D—Mediated Induction of Innate Immunity in Gingival Epithelial Cellis" Infection and Immunity, vol. 79, 2011, p. 2250-2256.

Dimeloe et al. "Regulatory T cells, inflammation and the allergic response the role of glucocorticoids and Vitamin D", Journal of Steroid Biochemistry & Molecular Biology, vol. 120, 2010, 86-95.

Barry, Robert, "The Power of Ubiquinol", The Key to Energy, Vitality, and a Healthy Heart, 2010, 5 pages.

Charig, et al., "CE3, Enamel Mineralization by Calcium-Containing Bicarbonate Toothpastes: Assessment by Various Techniques", Compendium, vol. 25, No. 9, pp. 14-31, Sep. 2004.

Lei, et al., "In Vitro Degradation of Novel Bioactive Polycaprolactone—20% Tricalcium Phosphate Composite Scaffolds for Bone Engineering", Materials Science and Engineering, vol. 27, No. 2, pp. 293-298, 2007.

(Continued)

*Primary Examiner* — H. Sarah Park
(74) *Attorney, Agent, or Firm* — Cozen O'Connor

(57) ABSTRACT

Topical, vitamin D, oral supplement compositions useful in treating oral inflammation comprising vitamin D in an aqueous-free emulsion containing a trans-oral mucosal absorption facilitator, where said emulsion forms a mucoadhesive coating in the presence of saliva; wherein saliva dissolution of the mucoadhesive gel releases vitamin D and the trans-oral mucosal, absorption facilitator; effecting: vitamin D passive diffusion; regulating in vivo availability and immune response of vitamin D; and maintaining adequate levels of circulating vitamin D while minimizing the risk of hypercalcemia.

12 Claims, No Drawings

(56) References Cited

OTHER PUBLICATIONS

Litkowski, et al., "CE4, Intraoral Evaluation of Mineralization of Cosmetic Defects by a Toothpaste Containing Calcium, Fluoride, and Sodium Bicarbonate", Compendium, vol. 25, No. 9, Sep. 2004.

Lowenstein, et al., "Vaterite: A Mineralization Product of the Hard Tissue of a Marine Organism (Ascidiacea)", Science, vol. 188, pp. 363-365, 1972.

Roveri, et al., "Surface Enamel Remineralization: Biomimetic Apatite Nanocrystals and Fluoride Ions Different Effects", Journal of Nanomaterials, vol. 2009, Article ID 746383, 9 pages.

Schemehorn, et al., "Remineralization by Fluoride Enhanced with Calcium and Phosphate Ingredients", Indiana University School of Dentistry, The British Library, Enamelon, Inc., Cranbury, NJ.

Tang, et al., "HPLC Analysis of Reduced and Oxidized Coenzyme Q10 in Human Plasma", Clinical Chemistry, vol. 47, No. 2, pp. 256-265, 2001.

Ten CATE, Jacob M., "Current Concepts on the Theories of the Mechanism of Action of Fluoride", Academic Centre for Dentistry Amsterdam (ACTA), Department of Cariology Endodontology Pedodontology, Amsterdam, The Netherlands, ACTA Odontol Scand, vol. 57, pp. 325-329, 1999.

Thies, C., "A Survey of Microencapsulation Processes", Washington University, St. Louis, MO.

Tung, et al., "CE2, Amorphous Calcium Phosphates for Tooth Mineralization", Compendium, vol. 25, No. 9 (Suppl 1), pp. 9-13, Sep. 2004.

Xu, et al., "Strong Nanocomposites with Ca PO4, and F Release for Caries Inhibition", J Dent Res, vol. 89, No. 1, pp. 19-28, 2010.

\* cited by examiner

TOPICAL VITAMIN D ORAL SUPPLEMENT COMPOSITIONS

RELATED APPLICATIONS

The subject application claims priority from U.S. Provisional Application Ser. No. 61/546,811 titled Dental Floss Containing Vitamin D Compound filed on Oct. 13, 2011, the entire content of which is incorporated by reference.

FIELD OF THE INVENTION

The subject application pertains to topical, vitamin D, oral supplement compositions useful in treating oral inflammation.

BACKGROUND OF THE INVENTION

Recent research has shown that human gingival epithelial cells (GEC) produce peptides, such as defensins and the cathelicidin LL-37, which are both antimicrobial and modulate the innate immune response. See: Diamond, G, et. al. (2008) "Hold defense peptides in the oral cavity and the lung: similarities and differences," *J. Dent. Res.* 87:915-927. Research has also demonstrated that these antimicrobial peptides are crucial in the prevention and control of periodontal disease of a bacteriological etiology. Specifically, these peptides have been shown to provoke an increased immune response and demonstrate antibacterial activity in the presence of the periodontal pathogen *Aggregaitbacter actinomycetemcomitans*. It has also been demonstrated that the genes responsible for the production of these antimicrobial peptides can be up-regulated or induced to produce an increased expression of these protective agents in the presence of adjunctively administered, vitamin D supplement, i.e. vitamin D3 [1,25(OH)2D3] and its precursors and derivatives. See: McMahone, L, et. al. (June 2011) "Vitamin D-mediated induction of innate immunity in gingival epithelial cells," *Infect. Immun.*, 79(6) 2250-7.

SUMMARY OF THE INVENTION

The present invention is directed to topical vitamin D oral supplement compositions useful in treating oral inflammation. Suitable vitamin D for the purposes of the invention include:
  Vitamin D,
  Vitamin D compounds with hydroxyl groups at 1, 3 and 25 carbon positions,
  esters of 1α,25-dihydroxy vitamin $D_3$,
  esters of 1,25-dihydroxy vitamin $D_3$,
  1,25 $(OH)_2D_3$ analogs of 1,25$(OH)_2D_3$,
  Calcitriol, 25$(OH)D_3$, analogs of 25$(OH)D_3$ and combinations thereof.

The vitamin D supplement is contained in aqueous-free emulsion along with a trans-oral mucosal, absorption facilitator.

The present invention is directed to a topical, vitamin D, oral supplement composition useful in treating oral inflammation comprising:
  a saliva soluble, aqueous-free, emulsion carrier;
  an effective level of vitamin D supplement; and
  a trans-oral mucosal, absorption facilitator, wherein:
    upon application to the oral mucosa, said composition forms a saliva soluble, mucoadhesive gel, substantive to said oral mucosa;
    upon continuous exposure of said saliva soluble, mucoadhesive gel to saliva flow, said mucoadhesive gel gradually dissolves effecting controlled release of said vitamin D supplement and said trans-oral mucosal, absorption facilitator onto said oral mucosa; and
    upon contacting said oral mucosa, said vitamin D supplement and trans-oral mucosal, absorption facilitator passively diffuse through said oral mucosa:
      (a) regulating the in vivo availability and immune response of vitamin D;
      (b) maintaining adequate levels of circulating vitamin D; and
      (c) minimizing risk of hypercalcemia.

Vitamin D supplement compositions of the invention, when topically applied to the oral mucosa in aqueous-free, emulsion compositions, form gels substantive to the oral mucosa. These gels gradually dissolve in the presence of saliva, releasing vitamin D and a trans-oral mucosal, absorption facilitator which, combined, effect passive diffusion of the vitamin D through the mucosa.

Incipient periodontal inflammation, gingivitis, is known to result from the inflammation reaction to the endotoxins released by the presence of bacterial biofilms in the general area of the tooth anatomy. Left untreated, this condition frequently progresses to the more virulent pathological condition known as periodontitis. It is believed that the frequent use of vitamin D, topical, supplement compositions of the invention provide protection by forming mucoadhesive gels that continuously release vitamin D composition at the inflamed site; thereby inducing passive diffusion of vitamin D into the mucosa which, in turn, increases production of the antimicrobial peptides and provokes a putative therapeutic immune modulating response.

The diffused vitamin D supplement maintains adequate levels of circulating vitamin D and regulates the in vivo availability and immune response of vitamin D, while minimizing the risk of hypercalcemia.

The Role of Vitamin D in Maintaining Periodontal Health in the Compositions of the Invention Periodontal diseases are initiated by a consortia of oral bacteria that elicit local inflammatory responses that lead to bleeding on probing, loss of periodontal attachment, as well as bone and tooth loss. They have been linked to systemic conditions, including heart disease, diabetes, obesity and metabolic syndrome. The association between periodontal diseases and these systemic conditions seems to be due to a low grade inflammatory burden that links them through a common pathophysiological mechanism. Conceivably, locally secreted cytokines and periodontal pathogens can enter into the bloodstream and contribute to damage elsewhere in the body and there appears to be some evidence for that burden.

Tumor necrosis factor α (TNF-α) and interleukin 6 (IL-6) are key cytokines in the initiation and maintenance of systemic inflammation which have been implicated in progression and severity of periodontitis. In addition, higher serum levels of these cytokines have been observed in periodontitis patients than in periodontally healthy individuals.

Leptin, adiponectin and resistin are adipokines that are secreted primarily by adipose tissues, but also produced by monocytes and macrophages and are able to directly influence inflammation. See: Teles, et. al. *Journal of Periodontology*, 2011.

Vitamin D has an important role in bone growth and maintenance, which might be beneficial for maintaining periodontal health. Recently, it has been suggested to have positive effects on periodontal diseases, tooth loss and gingival inflammation not through its effects on bone metabolism, but rather through anti-inflammatory mechanisms. Hence, maintaining adequate serum values of Vitamin D via topical, adjunctive, vitamin D supplement compositions could be important in the prevention and treatment of periodontal diseases.

Vitamin D has an important role in calcium homeostasis, bone growth and preservation. It has been shown to inhibit antigen-induced T cell proliferation and cytokine production, acting as an immunomodulatory agent.

Recently, vitamin D has been proposed to also have antiinflammatory properties. Analyzing 6,700 subjects (See: Dietrich, et. al., *Am. J. Clin. Nutr.* 2005, 82:575-580) found that individuals in the highest quintile of serum vitamin D presented significantly less bleeding, lower mean pocket depth and clinical attachment loss, number of missing teeth and BMI. It has also been suggested that vitamin D (and calcium) supplementation may have a positive effect on periodontal health, particularly on bleeding on probing, gingival index and PD.

See: Garcia, et. al. *J. Periodontol.* 82:25-32; and Miley, et. al. *J. Periodontol.*, 2009; 80:1433-1439.

Interestingly, polymorphisms in vitamin D receptors have been linked to generalized aggressive periodontitis (GAgP) (see: Park, et. al. *J. Clin. Periodontol.* 2006; 33:524-528) and severe chronic periodontitis (see: Wang, et. al. *J. Periodontol.* 2009; 80:603-608). The highest levels of circulating vitamin D were detected among the individuals that presented less bleeding on probing, lower mean PD, CAL and number of missing teeth, as well as levels of pathogenic bacteria. In addition, the proposed anti-inflammatory role of vitamin D was confirmed by its positive correlation with adiponectin and negative correlation with IL-6 and leptin.

The active form of vitamin D, 1,25-dihydroxyvitamin D3 [1,25(OH)2D3], is a secosteroid hormone that regulates calcium and bone metabolism, controls cell proliferation and differentiation and exerts immunoregulatory activities. This range of functions has been exploited clinically to treat a variety of conditions, from secondary hyperparathyroidism to osteoporosis, to autoimmune diseases such as psoriasis. Recent advances in understanding 1,25(OH)2D3 functions and novel insights into the mechanisms of its immunomodulatory properties suggest a wider applicability of this hormone in the treatment of oral inflammation.

The di-hydroxylated, biologically active form of vitamin $D_3$, also known as calcitriol, is a central hormone in calcium homeostasis and bone metabolism, but has also a number of other functions and notably powerful immunomodulatory properties, which are attractive for adjunctive, topical supplementation.

U.S. Pat. No. 5,952,317 discusses calcitriol derivatives and their uses. Calcitriol can be regulated to thus provide controlled release of vitamin D in vivo over time, by changing or modifying the hydrolysable groups. Structurally, the key feature of the modified vitamin D compounds having desirable biological attributes is that they are derivatives of 25-dihydroxyvitamin D3, or derivatives of 25-dihydroxyvitamin D analogs, in which a hydrolysable group is attached to the hydroxyl group of carbon 25 and, optionally, to any other of the hydroxyl groups present in the molecule. Depending on various structural factors, e.g. the type, size, structural complexity of the attached group, these derivatives are thought to hydrolyze to 25-dihydroxyvitamin D3, or to a 25-dihydroxyvitamin D3 analog, at different rates in vivo, thus providing for "slow release" of the biologically active vitamin D compound (i.e. 1,25-dihydroxyvitamin D3, or an analog thereof) in the body. The "slow release" in vivo activity profiles of such compounds can be further modulated by the use of mixtures of derivatives (e.g. mixtures of different derivatives of 1,25-dihydroxyvitamin D3, or different derivatives of 1,25-dihydroxyvitamin analogs) or the use of mixtures consisting of one or more vitamin D derivatives together with chemically modified molecules derived from 1,25(OH)2D3. Modifications have been made throughout the molecule to obtain analogs with the desired properties. More than 1000 different vitamin D analogs have been synthesized worldwide. All of these analogs fall within the description of vitamin D as discussed and claimed in the present invention.

Vitamin D receptor (VDR): a member of the superfamily of nuclear receptors for steroid hormones and retinoid acid. The VDR functions as a 1,25(OH)2D3-activated transcription factor that ultimately influences the rate of RNA polymerase mediated transcription. VDRs are present not only in cells typically involved in calcium and bone metabolism, but also in other cell types, such as cells of the immune system. See: Chantal Mathieu and Luciano Adorini. "The coming age of 1,25-dihydroxyvitamin D3 analogs as immunomodulatory agents," *TRENDS in Molecular Medicine*. Vol 8, No 4, April 2002.

An immunomodulatory role for vitamin D was first proposed more than 25 years ago, based on two salient observations. Firstly it was shown that monocytes/macrophages from patients with the granulomatous disease, sarcoidosis, constitutively synthesize the active form of vitamin D, 1,25-dihydroxyvitamin D (1,25(OH)$_2$D) from precursor 25-hydroxyvitamin D (25OHD). Secondly, the receptor for 1,25(OH)$_2$D (vitamin D receptor, VDR) is detectable in activated, proliferating lymphocytes. These observations suggested a mechanism whereby 1,25(OH)$_2$D produced by monocytes could act upon adjacent T-cells or B-cells, but the impact of such a system on normal immune system regulation was uncertain. Indeed, it is only in recent years that a much clearer picture of the role of vitamin D as a determinant of immune responsiveness has emerged. Two new concepts have prompted this change. Firstly studies of innate immunity have shown that intracine induction of antimicrobial activity by vitamin D is a pivotal component of monocyte/macrophage response to infection. Secondly, it is now clear that sub-optimal vitamin D status is a common feature of many populations throughout the world, with the potential to compromise monocyte/macrophage metabolism of 25OHD and subsequent actions of 1,25(OH)$_2$D. More recent reviews detail these new developments with specific reference to the metabolic and signaling mechanisms associated with innate immune regulation by vitamin D and implications for human disease. See: Martin Hewison, "Review: Vitamin D and the intracrinology of innate immunity," *Molecular and Cellular Endocrinology* 321 (2010) 103-111.

In a recent review of this subject Holick (2007) *N. Engl. J. Med.*, 357:266-281, indicated that vitamin D insufficiency could be characterized by circulating levels of 25OHD that were greater than vitamin D-deficiency (50 nM or 20 ng/m1) but less than 75 nM (30 ng/ml). See: Holick 2009, *Ann. Epidemiol.* 19: 73-7.

Thus, for the first time since the original sarcoidosis studies it is possible to propose a mechanism detailing the benefits of intracine metabolism of 25OHD with respect to innate immune response to infection by monocyte/macrophages. In the face of an immune challenge such as infection with M.tb. pathogen-sensing receptors such as TLRs trigger enhanced expression of 1α-hydroxylase and VDR. Provided there is sufficient 25OHD available, this will then elevate local levels of 1,25(OH)$_2$D, stimulating transcription of the hCAP gene, with the resulting antimicrobial protein being incorporated into lysosomes to promote bacterial killing. Initially hCAP was thought to act primarily by disrupting bacterial cell membranes. See: Nizet and Gallo, *Scan. J. Infect. Dis.*, 2003; 35:670-676.

A new perspective on the interaction between vitamin D and human immunity has shed light on the intracrine mechanisms that are central to its immunomodulatory activity. Crucially it is now clear that these mechanisms are also common to cells from a variety of tissues outside the classical immune system, notably "barrier" sites such as the skin, lungs, intestine, placenta and oral mucosa. Irrespective of the cell type involved in mediating intracrine responses to vitamin D, these studies have underlined the potential problems that may stem from inadequate vitamin D status. The latter appears to be a prevalent condition in communities throughout the world, further emphasizing the need for new clinical studies aimed at assessing the physiological and disease consequences of vitamin D insufficiency and the potential for topical administration of vitamin D supplement to local inflammatory conditions, as described and claimed in the present invention.

Vitamin D deficiency has been correlated with increased rates of infection. Since the early 19$^{th}$ century, both environment (i.e. sunlight) and dietary sources of vitamin D (i.e. cod liver) have been identified as treatments for TB. The recent discovery that vitamin D induces antimicrobial peptide gene expression explains, in part, the "antibiotic" effect of vitamin D and has greatly renewed interest in the ability of vitamin D to improve immune function. Subsequent work indicates that this regulation is biologically important for the response of the innate immune system to wound and infection, including oral infections, and that deficiency may lead to suboptimal responses toward bacterial and viral infections. The potential for topical supplementation of vitamin D to respond to oral inflammation is most promising.

25(OH)D circulates in the blood bound to the vitamin D-binding protein and is a reliable indicator of vitamin D status. To become fully activated, the 25(OH)D is converted into 1,25-dihydroxyvitamin D(1,25(OH)2D) by the mitochondrial 1α-hydroxylase enzyme (CYP2781). The majority of the body's 1,25(OH)2D is synthesized in the primary renal tubules of the kidney, but the synthesis also occurs in numerous extrarenal sites up to cells that express CYP2781.

The genomic actions of 1,25(OH)2D are modulated through the vitamin D receptor (VDR), a transcription factor belonging to the steroid/hormone receptor family.

Deficiency in vitamin D is associated with numerous health conditions ranging from bone health to cancer, but with the discovery of antimicrobial peptide gene regulation by the vitamin D pathway, a renewed interest in its impact on the immune system has ensued. It is particularly attractive to realize that adequate levels throughout life may alleviate many of the chronic ills that befall us as we age. "Local" vitamin D levels may be influenced by repetitive, topical administration of vitamin D supplement, throughout the day.

Many epithelial tissues such as the oral mucosa, intestinal tract, skin, urinary tract and reproductive organs are constantly exposed to the environment and the importance of the vitamin-D-cathelicidin pathway in providing protection against pathogens in these tissues is already a major focus. This includes topical application of vitamin D supplement to the oral mucosa from compositions that effect continuous trans-oral, mucosal absorption throughout the day, as disclosed and claimed in the present invention.

Considering that most people have insufficient levels of vitamin D and that nearly 1 billion people worldwide are deficient, properly designed supplementation studies in humans will be important for determining the benefits from raising serum levels of vitamin D. See: Adrian F. Gombart. The Vitamin D-antimicrobial peptide pathway and its role in protection against infection. *Future Microbial.* (2009) 4(9): 1151-1166.

Vitamin D is known to modulate calcium homeostasis and has a role in the regulation of electrolytes and blood pressure. There is now an increasing amount of evidence to show that $1,25(OH)_2D_3$, the most active metabolite of vitamin D, regulates the immune response and possesses anti-inflammatory activity. See: *Current Opinion in Gastroentarology.* 2010; 26:591-595.

Significant advances have been made in the characterization of vitamin D and the vitamin D receptor (VDR) in immune function. The studies of signaling pathways involved in the response to infection and inflammation have led to a more detailed understanding of the cellular response to vitamin D through VDR. The present invention is based on recent progress in understanding how vitamin D, topically administered to the oral mucosa, contributes to mucosal immune function, particularly in relation to the molecular mechanisms by which Vitamin D and VDR influence mucosa-immunity, bacterial infection, and inflammation.

Recently, it was shown that vitamin D modulates the T cell antigen receptor, further demonstrating that vitamin D has a nonclassical role in immunoregulation. The anti-inflammation and anti-infection functions for Vitamin D are newly identified and highly significant activities, relied on by the topical, vitamin D supplement compositions of the invention. Vitamin D/VDR have multiple critical functions in regulating the response to intestinal homeostasis, tight junctions, pathogen invasion, commensal bacterial colonization, antimicrobe peptide secretion and mucosal defense. Interestingly, microorganisms modulate the VDR signaling pathway.

Vitamin D is known as a key player in calcium homeostasis and electrolyte and blood pressure regulation. Recently, important progress has been made in understanding how the noncanonical activities of Vitamin D influence the pathogenesis and prevention of human disease. Vitamin D and VDR are directly involved in T cell antigen receptor signaling. The involvement of vitamin D/VDR in anti-inflammation and anti-infection represents a newly identified and highly significant activity for VDR. Studies have indicated that the dysregulation of VDR may lead to exaggerated inflammatory responses, raising the possibility of defects in vitamin D and VDR signaling transduction may be linked to bacterial infection and chronic inflammation including periodontitis.

Overall, the effects of $1,25(OH)_2D_3$ on the immune system include: modulating the TCR, decreasing Th1/Th17CD4+ T cells and cytokines, increasing regulatory T cells, downregulating T cell-driven production and inhibiting dendritic cell differentiation.

Consistent with its anti-inflammatory role, $1,25(OH)_2D_3$ downregulates the expression of many proinflammatory cytokines, such as IL-1, IL-6, IL-8 and TNF-α, in a variety of cell types. Immune cells, including macrophages, dendritic cells and activated T cells, express the intracellular VDR and are responsive to $1,25(OH)_2D_3$.

Vitamin D deficiency has been correlated with increased rates of infection. Moreover, $1,25(OH)_2D_3$ induces the expression of antimicrobial peptides, such as carthelicidin. Thus, recent studies have greatly renewed interest in the anti-infection activity of $1,25(OH)_2D_3$ for use in the topical, supplement compositions of the invention. See: Gombert A. F. *Future Microbial.* 2009; 4:1151-1165.

Manipulating the level of $1,25(OH)_2D_3$ in the body and restoring the function of VDR via topical supplementation represent a new approach to treating periodontitis, relied on by the topical supplement compositions of the invention. 1,25(OH)$_2$D$_3$ has potent immunomodulatory properties that have promoted its potential use in the prevention and treatment of infectious disease, including periodontitis. See: Newsson M. *Mol. Cell Endocrinol.* 2010; 321:103-111.

Vitamin D deficiency at the time of periodontal surgery negatively affects treatment outcomes for up to 1 year. Analysis of data suggests that vitamin D status may be critical for post-surgical healing. (Clinical)Trials.gov number, CT00277065.

The primary sources of vitamin D are dietary intake and sunlight exposure in the form of vitamin D2 and D3, which are metabolized to 25-hydroxyvitamin D [25(OH)D] in the liver. Further metabolism in the kidneys produces the active form of vitamin D, 1,25-dihydroxyvitamin D.

Periodontitis is characterized by alveolar bone loss induced by the host immune response in bacterial insult. Because vitamin D plays a crucial role in bone maintenance and immunity, there is biologic rationale to suspect that a vitamin D deficiency could negatively affect the periodontium. A diagnosis of vitamin D deficiency is made through serum analysis of 25(OH)D levels. The normal range of serum 25(OH)D levels is 20-74 ng/mL. No absolute threshold for deficiency status is universally accepted, although most authorities agree that levels below 20-30 ng/mL constitute at least a mild deficiency with severe vitamin D deficiency beginning at a level of 12 ng/mL. See: Bashutski, et. al. *J. Dent. Res.* 90(8). 1007-1012, 2011. Topical supplementation of vitamin D in the compositions of the invention, influence "local" vitamin D levels of cells under challenge.

In cross-sectional studies, low vitamin D levels have been associated with increased gingival inflammation, tooth loss, clinical attachment loss and material periodontal disease during pregnancy. Daily administration of vitamin D via topical supplement compositions of the invention are projected to increase "local" vitamin D levels.

Interestingly, vitamin D supplementation at the time of surgery fails to prevent the negative clinical outcomes associated with baseline deficiency. Patients were supplemented with a vitamin D for only a six-week period, and it takes up to 3 months for serum 25(OH)D levels to stabilize after vitamin D intake is increased. See Veith R, et. al. *Am. J. Clin. Nutr.* 2001 February; 73(2):288-94. Six-week vitamin D supplementation alone did not exert long-term effects, since serum 25(OH)D levels returned to baseline levels in placebo patients by 6 months.

Analysis of data suggests that if an individual is vitamin D-deficient, minimal benefits can be obtained from periodontal surgery. Furthermore, vitamin D supplementation at the time of surgery is unable to prevent this effect. Since vitamin D deficiency is highly prevalent, it may be advisable to ensure adequate vitamin D levels well in advance of periodontal surgery, to attain the best possible results. Oral vitamin D supplementation, combined with topical vitamin D supplement compositions of the invention, administered daily for an extended period prior to periodontal surgery, is recommended.

Epidemiological studies suggest that low vitamin D levels may increase the risk or severity of respiratory viral infections. One study examined the effect of vitamin D on respiratory syncytial virus (RSV)-infected human airway epithelial cells. Airway epithelium converts 25-hydroxyvitamin D$_3$ (storage form) to 1,25-dihydroxyvitamin D$_3$ (active form). Active vitamin D generated locally in tissues, is important for the nonskeletal actions of vitamin D, including its effects on immune responses. It was found that vitamin D induces IkBα, an NF-kB inhibitor, in airway epithelium and decreases RSV induction of NF-kB-driven genes such as IFN-β and CXCL10. It was also found that exposing airway epithelial cells to vitamin D reduced induction of IFN-stimulated proteins with important antiviral activity (e.g., myxovirus resistance A and IFN-stimulated protein of 15 kDa). In contract to RSV-induced gene expression, vitamin D had no effect on IFN signaling, and isolated IFN induced gene expression. Inhibiting NF-kB with an adenovirus vector that expressed a nondegradable form of IkBa mimicked the effects of vitamin D. When the vitamin D receptor was silenced with small interfering RNA, the vitamin D effects were abolished. Most importantly it was found that, despite inducing IkBa and dampening chemokines and IFN-β, there was no increase in viral mRNA or protein or in viral replication.

It can be concluded that vitamin D decreases the inflammatory response to viral infections in airway epithelium without jeopardizing viral clearance. This suggests that adequate vitamin D levels would contribute to reduced inflammation and less severe disease in RSV-infected individuals.

Vitamin D is increasingly recognized as a pluripotent hormone with functions that extend beyond its classical role in calcium homeostasis. Rapidly growing evidence from epidemiological and basic research studies reveals that vitamin D can modulate immune responses. Vitamin D deficiency is highly prevalent and has been associated with both increased risk of several inflammatory diseases and susceptibility to infections, including periodontitis. The localized tissue-specific generation of active vitamin D is thought to be a key component of nonclassical vitamin D functions that are relied on by the supplement compositions of the invention. Previously published data has shown that normal lung epithelium constitutively converts 25-hydroxyvitamin D$_3$ (storage form of vitamin D) to 1,25-dihydroxyvitamin D$_3$(1,25D) (active form of vitamin D) and that the generation of active vitamin D is increased in the presence of viral infection.

Inflammation is an essential component of host defense; however, a too vigorous response against microbes or inflammation may be deleterious to the host, leading to impaired organ function. Vitamin D has been shown to inhibit production of inflammatory chemokines in animal models of inflammatory diseases such as multiple sclerosis and type 1 diabetes.

The family of NF-kB transcriptional regulatory factors has a central role in coordinating the expression of a wide variety of genes that control immune responses. NF-kB proteins are present in the cytoplasm in association with 1 kBs. IkBs are phosphorylated by IkB kinase following cell stimulation, and they are targeted for destruction by the ubiquitin/proteasome degradation pathway. The degradation of IkB allows NF-kB proteins to translocate to the nucleus, bind to their DNA binding sites and activate a variety of genes. See: Sif Hansdottir, et. al., *The Journal of Immunology.* 2010; 184: 965-974.

The hormonal form of vitamin D up-regulates antimicrobial peptides, namely cathelicidin, to enhance clearance of bacteria at various barrier sites and in immune cells. Vitamin D modulates the adaptive immune system by direct effects on T cell activation and on the phenotype and function of antigen-presenting cells (ACPs), particularly of DCs.

The importance of vitamin D on the regulation of cells in the immune system has gained increased appreciation over the past decade with the discovery of the vitamin D receptor (VDR) and key vitamin D metabolizing enzymes expressed by cells of the immune system. Animal studies, early epidemiologic and clinical studies have supported a potential role for vitamin D in maintaining immune system balance.

It is currently believed that vitamin D enhances innate immunity by up-regulating antimicrobial peptides such as cathelicidin in response to infection. This up-regulating of antimicrobial peptides is relied on by the topical supplement compositions of the present invention.

Therefore, antimicrobial peptides such as cathelicidin constitute an integral part of the innate immune response to a variety of infections especially at barrier sites, such as oral mucosa.

Taken together, these findings suggest that $1,25(OH)_2D_3$ up-regulates antimicrobial peptide production, primarily cathelicidin, on a variety of different cells and can be relied on in the vitamin D supplement compositions of the present invention.

In summary, the effects of $1,25(OH)_2D$ on the immune system include decreasing Th1/Th17 CD4+ T cells and cytokines, increasing regulatory T cells, downregulation of T cell-driven IgG production and inhibition of dendritic cell differentiation. While enhancing protective innate immune responses, $1,25(OH)_2D$ helps maintain self-tolerance by dampening overly zealous adaptive immune responses. See: Diane L. Kamen and Via Taagpricha. Vitamin D and molecular actions on the immune system: modulation of innate and autoimmunity. *J. Mol. Med.* (2010) 88:441-450.

Vitamin D, administered by topical supplement compositions of the invention, may be beneficial for the treatment of periodontal disease, an inflammatory condition involving activation of host-defense cells by bacterial release of inflammatory mediators, which results in the destruction of supporting periodontal tissues, including connective tissue and alveolar bone.

Third National Health and Nutrition Examination Survey (NHANES III), which included 12,000 adults, revealed significant associations between periodontal health and vitamin D and calcium intakes. Thus, data from this large cohort would support the hypothesis that lower dietary intakes of vitamin D and calcium may contribute to poor periodontal health in a dose-dependent fashion.

Periodontal health improves in patients attending regular periodontal care programs, regardless of their dietary calcium or vitamin D supplements. However, taking calcium and vitamin D supplementation is associated with better periodontal health relative to taking no such supplements. Previous reports had suggested that vitamin D may reduce the susceptibility to gingival inflammation through anti-inflammatory effects, and one study demonstrated an inverse linear association between 25(OH)D and BOP. Consistent with this report, it was observed less BOP and less inflammation in supplement takers, a difference that was evident at baseline and remained significant for 1 year while subjects underwent periodontal maintenance therapy. It should be noted that because of the inclusion of different covariates, the results of baseline analysis reported here are slightly different from those reported previously in the same population. See: M. Nathalia Garcia, et. al. One-Year Effects of Vitamin D and Calcium Supplementation on Chronic Periodontitis. *J. Periodontol.* 2011; 82:25-32.

Optimal levels of vitamin D should have an immunosuppressive effect on periodontal disease. See: D. Dixon, et. al. Calcium and vitamin D use among adults in periodontal disease maintenance programmes. *British Dental Journal.* 2009: 208:827-831.

In addition to its action on skeletal homeostasis, vitamin D and, in particular, its hormonally active form, $1\alpha,25$-dihydroxyvitamin D, has anti-inflammatory and antimicrobial effects via modulation of inflammatory cytokine production by immune cells and stimulated secretion of peptides with antibacterial action by cells of the monocyte-macrophage lineage. These properties lend themselves to topical supplement compositions for treatment of "local" oral infections.

All of the clinical and radiographical measurements indicate better periodontal health for subjects who took oral vitamin D and calcium supplementation. Furthermore, because all of the subjects were enrolled in periodontal maintenance programs, the data are consistent with the notion that taking vitamin D and calcium supplements may be beneficial effects above and beyond those of standard periodontal care.

Results suggest that vitamin D and calcium supplementation could be advocated as a component of periodontal disease management. See: D. Douglas, et. al., *J. Periodontol.* September 2009; 80:1433-1439.

Resulting recommendations vary widely. However, vitamin D likely has beneficial effects on various outcomes other than bone health, such as muscle strength, colon cancer and inflammatory diseases. In the present study, no evidence was found for a threshold serum concentration of 25(OH)D, above which the association with gingival inflammation leveled off. Hence, the anti-inflammatory effects of vitamin D may possibly extend to serum concentration of 90-100 nmol/L. These results are consistent with an anti-inflammatory effect of vitamin D on gingival inflammation which may be an alternative pathway by which vitamin D may be beneficial for the prevention of periodontal disease.

Vitamin D may reduce susceptibility to gingival inflammation through its anti-inflammatory effects. Gingivitis may be a useful clinical model to evaluate the anti-inflammatory effects of vitamin D. See: Thomas Dietrich, et. al. *Am. J. Clin. Nutr.* 2005; 82-575

DETAILED DESCRIPTION OF THE PRESENTLY PREFERRED EMBODIMENTS

In a preferred topical, vitamin D, oral supplement composition of the invention, vitamin D supplement enhances innate immunity by upregulating the antimicrobial peptide, cathelicidin.

In a preferred embodiment of the invention, the topical, vitamin D, oral supplement composition, in its hormonally active form, $1\alpha,25$-dihydoxyvitamin D, indicates anti-inflammatory and antimicrobial effects via modulation of inflammatory cytokine production, by stimulating secretion of antibacterial properties. A topical, vitamin D, oral supplement composition, and said hormonally active-form, $1\alpha,25$-dihydoxyvitamin D, calcitriol, indicates immunomodulatory properties.

In a preferred embodiment of the invention, a topical, vitamin D, oral supplement composition, the anti-inflammatory and antimicrobial effects of $1\alpha,25$-dihydoxyvitamin D are modulated through vitamin D receptor (VDR).

In a preferred embodiment of the invention, the topical, vitamin D, oral supplement composition, the $1\alpha,25$-dihydoxyvitamin D effects on the immune system include:
modulating TCR,
decreasing TH1/TH17/CD4 and T cells and cytokines
increasing regulatory T cells
down regulating T cell-driven production, and
inhibiting dendritic cell differentiation
The present invention includes methods:
for treating oral inflammation comprising topically administering a vitamin D supplement composition to the oral mucosa comprising:
a saliva soluble, aqueous-free emulsion carrier;
an effective level of vitamin D supplement; and
a trans-oral mucosal, absorption facilitator, wherein:

upon application to the oral mucosa, said composition forms a saliva soluble, mucoadhesive gel, substantive to said oral mucosa;

upon continuous exposure of said saliva soluble, mucoadhesive gel to saliva flow, said mucoadhesive gel gradually dissolves effecting controlled release of said vitamin D supplement and said trans-oral mucosal, absorption facilitator onto said oral mucosa;

wherein application means for said topical vitamin D oral supplement composition is selected from the group consisting of interproximal devices coated with said composition, oral gels, oral ointments, oral pastes, oral varnishes, oral liquids and combinations thereof;

wherein treating oral inflammation comprises topically administering vitamin D supplement compositions is applied repetitively throughout the day with a vitamin D supplement gel in combination with daily topical administration with a dental device coated with said composition.

Vitamin D compositions, suitable for topical administration to the oral mucosa, include: an aqueous-free emulsion carrier for the vitamin D that also contains trans-oral mucosal absorption facilitators, wherein said aqueous-free emulsion, upon exposure to saliva, forms a mucoadhesive gel substantive to the oral mucosa. Upon saliva dissolution of this mucoadhesive gel, the vitamin D/trans-oral mucosal, absorption facilitator mixture gradually releases from the mucoadhesive gel to passively diffuse through the oral mucosa, thereby supplementing system serum levels of vitamin D.

Topical administration of the vitamin D compositions of the invention to the oral mucosa is preferably carried out with oral gels or dental devices coated with the vitamin D composition. Particularly preferred, topical administration of vitamin D to the oral mucosa is effected by a combination of several administrations of vitamin D supplement topical gel throughout the day, combined with once or twice daily flossing with a dental device composition coated with the vitamin D composition of the invention.

For purposes of the present invention, saliva soluble, aquous-free emulsions include those emulsions that are comprised of polydimethylsiloxane in a nonionic surfactant, as described in the following U.S. Pat. Nos. 5,032,387; 5,098,711; 5,538,667 and 5,651,959; all of which are hereby incorporated by reference.

Preferred nonionic surfactants of the invention capable of forming a mucoadhesive gel in the presence of saliva. These are selected from the group consisting of: poloxamer 237, poloxamer 338, poloxamer 407 and combinations thereof.

For the purposes of the present invention, trans-oral mucosal, absorption facilitators are selected from the group consisting of: dexpanthenol, d-Limonene, poloxamer, PEG, benzyl alcohol, carbopol, chitosan, N-trimethylchitosan, menthol and combinations thereof.

Preferred aqueous-free, saliva soluble emulsions for use as carriers of vitamin D supplement compositions of the present invention include emulsions of polydimethylsiloxane (PDMS) at viscosities ranging from between about 1500 cs and about 2.5 million cs. Particularly preferred, aqueous-free emulsions include as the discontinuous phase PDMS at viscosities between 10,500 cs and 2.5 million cs with those nonionic surfactants described in detail in U.S. Pat. No. 5,651,959, as the continuous phase.

Preferred polydimethylsiloxanes are selected from the group consisting of polydimethylsiloxane: at 1500 cs, at 12,500 cs, at 100,000 cs, at 250,000 cs, at 500,000 cs, at 750,000 cs, at 1.5 million cs, at 2.2 million cs, at 2.5 million cs and combinations thereof.

Preferred application means for the topical vitamin D oral supplement compositions of the present invention include: oral gels, oral ointments, oral pastes, oral varnishes, oral liquids and various interproximal devices coated with said topical vitamin D oral supplement compositions.

Preferred oral gels for purposes of the present invention include those gels disclosed in U.S. Pat. Nos. 5,009,881; 5,032,387; 5,057,306; 5,057,307; 5,057,309; 5,538,667 and 5,651,959; all of which are included herein by reference.

Preferred coated, interproximal devices, suitable for releasing vitamin D oral supplement compositions interproximally, include those interproximal devices described in the following U.S. Pat. Nos. 4,911,927; 4,942,034; 5,098,711; 5,165,913; 5,665,374; 5,711,935; 6,545,077; 6,575,176; 7,017,591; 7,025,986 and 7,152,611; all of which are hereby included by reference.

The use of dental devices is an extremely important adjunct to proper dental hygiene. Dental devices have long been used effectively to clean the spaces between the teeth and under the gingival margin. When used properly, dental devices have been found to be effective in inhibiting tooth decay and gum disease. They are recommended by dentists for daily dental hygiene.

To increase the effectiveness of the dental devices, some devices have included certain medicinal ingredients or dentifrice components to help protect the tooth enamel from acid attack. Bactericides have also been used in connection with dental floss to inhibit periodontal disease.

The vitamin D supplement compositions in the dental devices of the invention can also be used in tandem and coated with salts containing ions known to inspire remineralization of hydroxyapatite tooth structure. Such compounds include: calcium, phosphorus and fluorine salts in forms such as dentifrices. Examples of such salts include, but are not limited to, fluoride or fluoride-containing compounds such as sodium fluoride, potassium fluoride, ammonium fluoride, sodium difluoride, potassium difluoride, ammonium difluoride, sodium silicofluoride, zinc fluoride, and stannous fluoride. Other dentifrices include, for example, ureases, acid phosphates, calcium carbonate, and magnesium carbonate. Examples of the acid phosphates which may be used include, for example, orthophosphoric acid, monosodium phosphate, monopotassium phosphate, disodium phosphate, dipotassium phosphate, monoamonium phosphate, hemisodium phosphate and sodium hexametaphosphate salts. The dentifrice is preferably included in the dental device in the amount sufficient to provide an effective, topical concentration at the tooth surface.

Other active components which may be incorporated within the interproximal device include hydrogen peroxide or other peroxide-producing components such as $PVP/H_2O_2$ or Carbamide peroxide, Fluoride, tooth acidulating agents such as buffered or acidulated phosphofluoride, sodium monofluorophosphate, plaque control agents, tartar control agents, antibiotics to treat pyorrhea and gingivitis, teeth whitening and bleaching agents, pH buffering agents, antifungal agents, remineralizing agents, hemostatic agents, immunological agents and nonionic and cationic antibacterials such as benzothonium chloride, acetyl trimethyl ammonium bromide, sanguinaria, triclosan (nonionic), tetracycline, cetyl pyridinium chloride and benzythonium chloride.

Additional active components that can be included in the dental devices of the present invention include Vitamin A, surfactants and pharmacological agents such as anti-cancer agents, stimulants, bone growth agents, antigens, hormones, steroids, anti-inflammatory agents and analgesic agents.

In other embodiments, the dental device comprises a coagulant to inhibit any bleeding which may be produced by flossing. Preferably, the coagulant is mixed in the device coating so as to directly contact the gum tissue. The coagulants may include vitamin K, calcium ions in the form of water-soluble calcium salts and blood factors that initiate the coagulation cascade. Alternatively, the coagulants may be solubilized in non-toxic solvents, such as ethanol, polyethylene terepthalate or diethyl ether.

Flavorants may be added to the dental devices of the present invention by techniques known in the art, such as adding the flavorant directly to the device after extrusion or by applying a flavored coating to the surface of the device, or by transferring volatile flavors to the device from a flavor reservoir. Known flavorants such as mint, cinnamon and bubble gum, which are commercially available through various suppliers including IFF Corporation, Dayton, N.J.; are suitable for use in the dental devices of the present invention. Other flavorants may also be added by the compression coating process described in the references cited.

Colorants may be added to the dental devices of the present invention to color the dental device in order to provide a visual stimulus to the consumer. Colorant can be added to the nylon or other pellets used to form the strand before extrusion begins. Any one of commercially available, FDA approved colorants for use with nylon resins may be used. Colors may correspond to the flavor of the dental device, e.g., red for cinnamon or green for mint. Further, multiple colors may be extruded simultaneously so that, for example, one side of the filament is red and other green. The device may further incorporate colorant agents or fluorescent dye to identify residual plaque deposits, such as, for example, FD&C Red 3 and FD&C Red 4.

ILLUSTRATIVE EXAMPLES

The invention is further described by the enclosed illustrative examples of topical gels and dental tape used to apply the vitamin D compositions of the invention to the oral mucosa and to interproximal surfaces, respectively.

Example 1

Topical Oral Gel with Calcitriol

A 500 mL stainless steel beaker was fitted with an overhead stirrer. Water, 135.834 gm, was added and moderate stifling began. The additional ingredients for this vessel were added. Sorbitol 70%, 102 gm; glycerin, 15 gm; potassium sorbate, 0.45 gm; sodium saccharin, 0.225 gm; sucralose, 0.6 gm, and flavors, 0.9525 gm, were added with moderate stifling at room temperature.

A 100 m beaker containing an aqueous-free emulsion [poloxamer 407/polydimethylsiloxane (2.5 million cs)] (90:10) 9.54 gm, was heated to 95 degrees C. with magnetic stirring. Calcitriol, 0.15 gm, was added to the beaker under a nitrogen blanket.

To a 50 mL beaker, with magnetic stifling and heating, was added propylene glycol, 30 gm, and methyl paraben, 0.45 gm. When the temperature attained 50 degrees C., carboxymethylcellulose 9H4XF, 4.65 gm, was added slowly over 3 minutes. After 5 minutes of stirring, the contents were added slowly to the 100 mL beaker, containing the aqueous-free emulsion. After continued stirring and cooling to 40 degrees C., the contents were added to the stainless steel beaker slowly over 3 minutes. After an additional 20 minutes the topical oral gel was packaged for topical dispensing from tubes under a head of nitrogen.

Example 2

Vitamin D PROPHY TAPE®

A 2 gallon stainless steel vessel was fitted with an overhead stirrer and placed on a hotplate. An aqueous-free emulsion [poloxamer 407/polydimethylsiloxane (12,500 cs)] (90:10) 1964 gm, was placed in the vessel and melted while stifling. The temperature rose to 90 degrees C. and the following ingredients were added: Pluracare L-1220, 120 gm; stearyl alcohol, 600 gm; microwax ML445 and polyethylene glycol 8000 were added to the molten aqueous-free emulsion. A homogenizer was placed in the vessel and emulsification resulted from 10 minutes of action. The following ingredients were then added with stifling: dicalcium phosphate dihydrate, dentifrice grade, 240 gm; propyl gallate, 4 gm; sodium saccharin, 72 gm; EDTA, 8 gm. Finally, calcitriol, 2 gm, was added to the emulsified coating composition. The emulsified tape coating batter was then dispensed into the tape coating tank. Compression coating of ultra-high-molecular-weight polyethylene dental tape, followed by overcoating with a SOFT ABRASIVES® bioglass, was completed; producing a saliva soluble, compression coated, dental tape with vitamin D and SOFT ABRASIVES® overcoating. This dental tape was packaged in paper-wrapped, single pieces, 20 inches in length. The single pieces of PROPHY TAPE® were packaged in flavor-sealed packaging accompanied by a flavor reservoir to which approximately 20 drops of volatile flavor was added.

What is claimed is:

1. A vitamin D composition useful in topically treating oral inflammation comprising:
  a saliva-soluble, aqueous-free emulsion carrier; wherein said saliva-soluble, aqueous-free emulsion carrier comprises polydimethylsiloxane selected from the group consisting of polydimethylsiloxane at 1500 cs, at 12,500 cs, at 100,000 cs, at 250,000 cs, at 500,000 cs, at 750,000 cs, at 1.5 million cs, at 2.2 million cs, at 2.5 million cs and combinations thereof which is emulsified in a non-ionic surfactant that is capable of forming a mucoadhesive gel in the presence of saliva; wherein said nonionic surfactant is selected from the group consisting of poloxamer 237, poloxamer 338, poloxamer 407 and combinations thereof;
  a therapeutically effective level of vitamin D; and
  a trans-oral mucosal absorption facilitator selected from the group consisting of dexpanthenol, d-Limonene, poloxamer, polyethylene glycol (PEG), benzyl alcohol, cross-linked polyacrylic acid, chitosan, N-trimethylchitosan, menthol and combinations thereof,
  wherein the saliva-soluble, aqueous-free emulsion carrier and/or trans-oral mucosal absorption facilitator comprises a poloxamer and said composition is aqueous free; and
  wherein:
    upon application to the oral mucosa, said composition forms a saliva-soluble, mucoadhesive gel, substantive to said oral mucosa;
    upon continuous exposure of said saliva-soluble, mucoadhesive gel to saliva flow, said mucoadhesive gel gradually dissolves effecting controlled release of said vitamin D and said trans-oral mucosal-absorption facilitator onto said oral mucosa; and upon contacting said oral mucosa, said vitamin D and trans-oral mucosal absorption facilitator passively diffuse through said oral mucosa:
(a) regulating the in vivo availability and immune response of vitamin D;
(b) maintaining adequate levels of circulating vitamin D; and
(c) minimizing the risk of hypercalcemia.

2. The composition according to claim 1, wherein said vitamin D is selected from the group consisting of:
a Vitamin D compounds with hydroxyl groups at the 1, 3 and 25 carbon positions,
an ester of $1\alpha,25$-dihydroxy vitamin $D_3$,
an ester of 1,25-dihydroxy vitamin $D_3$,
$1,25(OH)_2D_3$,
Calcitriol, $25(OH)D_3$, an analog of $25(OH)D_3$, and combinations thereof.

3. The composition according to claim 1, wherein application means for said composition is selected from the group consisting of interproximal devices coated with said composition, oral gels, oral ointments, oral pastes, oral varnishes, oral liquids and combinations thereof.

4. The composition according to claim 3, wherein said interproximal device application means is selected from the group consisting of compression coated: dental tape, multifilament or monofilament dental floss or interproximal devices, coated one-handed: dental devices, dental picks, dental stimulators and combinations thereof.

5. The composition according to claim 1, wherein said vitamin D enhances innate immunity by upregulating the antimicrobial peptide cathelicidin.

6. The composition according to claim 1, wherein said vitamin D is $1\alpha,25$-dihydoxyvitamin D.

7. The composition according to claim 6, wherein said $1\alpha,25$-dihydoxyvitamin D is calcitriol.

8. The composition according to claim 7, wherein said $1\alpha,25$-dihydoxyvitamin D's effects on the immune system include:
modulating TCR;
decreasing TH1/TH17/CD4 and T cells and cytokines;
increasing regulatory T cells;
down regulating T cell-driven production; and
inhibiting dendritic cell differentiation.

9. A method for treating oral inflammation comprising topically administering to the oral mucosa a vitamin D supplement composition comprising:
a saliva-soluble, aqueous-free emulsion carrier; wherein said saliva-soluble, aqueous-free emulsion carrier comprises polydimethylsiloxane selected from the group consisting of polydimethylsiloxane at 1500 cs, at 12,500 cs, at 100,000 cs, at 250,000 cs, at 500,000 cs, at 750,000 cs, at 1.5 million cs, at 2.2 million cs, at 2.5 million cs and combinations thereof which is emulsified in a nonionic surfactant that is capable of forming a mucoadhesive gel in the presence of saliva; wherein said nonionic surfactant is selected from the group consisting of poloxamer 237, poloxamer 338, poloxamer 407 and combinations thereof;
a therapeutically effective level of vitamin D; and
a trans-oral mucosal absorption facilitator selected from the group consisting of dexpanthenol, d-Limonene, poloxamer, polyethylene glycol (PEG), benzyl alcohol, cross-linked poly acrylic acid, chitosan, N-trimethylchitosan, menthol and combinations thereof,
wherein the saliva-soluble, aqueous-free emulsion carrier and/or trans-oral mucosal absorption facilitator comprises a poloxamer and said composition is aqueous free; and
wherein:
upon application to the oral mucosa, said composition forms a saliva-soluble, mucoadhesive gel, substantive to said oral mucosa;
upon continuous exposure of said saliva-soluble, mucoadhesive gel to saliva flow, said mucoadhesive gel gradually dissolves effecting controlled release of said vitamin D and said trans-oral mucosal-absorption facilitator onto said oral mucosa; and
upon contacting said oral mucosa, said vitamin D and trans-oral mucosal absorption facilitator passively diffuse through said oral mucosa:
(a) regulating the in vivo availability and immune response of vitamin D;
(b) maintaining adequate levels of circulating vitamin D; and
(c) minimizing the risk of hypercalcemia.

10. A method, according to claim 9, wherein said vitamin D supplement is selected from the group consisting of:
Vitamin D,
Vitamin D compounds with hydroxyl groups at 1, 3 and 25 carbon positions,
esters of $1\alpha,25$-dihydroxy vitamin $D_3$,
esters of 1,25-dihydroxy vitamin $D_3$,
$1,25(OH)_2D_3$ analogs of $1,25(OH)_2D_3$,
Calcitriol, $25(OH)D_3$, analogs of $25(OH)D_3$ and combinations thereof.

11. A method, according to claim 9, wherein application means for said topical vitamin D oral supplement composition is selected from the group consisting of interproximal devices coated with said composition, oral gels, oral ointments, oral pastes, oral varnishes, oral sealants, oral rinses, oral liquids and combinations thereof.

12. A method for treating oral inflammation comprising topically administering vitamin D supplement compositions, according to claim 9, wherein said composition is applied repetitively throughout the day with a vitamin D supplement gel in combination with daily topical administration with a dental device coated with said composition.

* * * * *